United States Patent [19]

Baum et al.

[11] 4,221,736
[45] Sep. 9, 1980

[54] BIS-(3,3-DINITROBUTYL)-POLYSILOXANE

[75] Inventors: Kurt Baum, Pasadena; Duane A. Lerdal, Sierra Madre, both of Calif.

[73] Assignee: The United States of America as represented by the Secretary of the Navy, Washington, D.C.

[21] Appl. No.: 933,366

[22] Filed: Aug. 14, 1978

[51] Int. Cl.$^2$ .............................................. C07F 7/10
[52] U.S. Cl. ...................................... 556/422; 149/88
[58] Field of Search ................................. 260/448.2 N

[56] References Cited

U.S. PATENT DOCUMENTS 4,139,403   2/1979   Baum et al. ............. 260/448.2 N X Primary Examiner—Paul F. Shaver
Attorney, Agent, or Firm—R. S. Sciascia; W. Thom Skeer; L. E. K. Pohl

[57] ABSTRACT

A method for producing an explosive ingredient bis-(3,3-dinitrobutyl)-polysiloxane is described.

11 Claims, No Drawings

BIS-(3,3-DINITROBUTYL)-POLYSILOXANE

BACKGROUND OF THE INVENTION

This invention relates to polysiloxanes and more particularly polynitrosiloxanes. The invention also relates to explosives and the use of polysiloxanes as explosives. The invention also relates to methods of preparation of polynitrosiloxanes.

Nitropolysiloxanes have shown promise as explosives and propellants. They combine the useful properties of polysiloxanes and the explosive activity of nitro compounds.

Prior attempts to form nitrated polysiloxanes have met with varying degrees of success. U.S. Pat. No. 2,756,246 describes a method of producing nitrooximes by reacting nitrogen dioxide with unsaturated siloxanes. This method does not produce the dinitro compounds. The dinitro compounds have a better oxygen balance and are more satisfactory explosives.

Organosiloxane nitrates have been produced according to the teaching in U.S. Pat. No. 3,222,319 by reacting trichloronitrate siloxanes with water and polymerizing the product of the reaction. This method appears unsuitable for the production of dinitrosiloxanes.

The synthesis of (3-fluoro-3,3-dinitropropyl)methylpolysiloxanes and bis(3-fluoro-3,3-dinitropropyl)-polysiloxane by the stepways introduction of nitro groups and fluorines by displacement reactions, oxidative nitrations and fluorinations is known. This method however has proven unsatisfactory for the production of internal gem dinitro groups.

SUMMARY OF THE INVENTION

The present invention comprises the reaction of diphenylsilane with allyl compounds in the presence of tris(triphenylphosphine)rodium chloride or other effective catalyst. The reaction product was reacted with water and methyllithium in ether to yield bis(3-hydroxybutyl)diphenylsilane. Reaction of this alcohol with phosphorus tribromide in ether yielded $(C_6H_5)_2Si(CH_2CH_2CHBrCH_3)_2$. Subsequently dephenylation with bromine was similar to that of the analogous fluorodinitropropyl compound. A cyclic polysiloxane with a molecular weight in the range of 800 to 2200 was produced by brominating this compound in acetic acid solvent with water added to complete bromination and hydrolysis.

DESCRIPTION OF THE PREFERRED EMBODIMENT

The starting material was obtained by a sequence of reactions beginning with the hydrosilylation of acrolein dimethyl acetal with diphenylsilane. The hydrosilylation of acrolein, as well as α,β-unsaturated ketones and esters, with triethylsilane has been reported to take place by 1,4-addition, yielding enol silyl ethers. However, acrolein acetal and triethylsilane in the presence of chloroplatinic acid gave, after hydrolysis, 3(triethylsilyl)propionaldehyde. For the addition of diphenylsilane to allyl compounds, tris(triphenylphosphine)rhodium chloride was found to be a more effective catalyst than chloroplatinic acid. Under these conditions, the adduct of acrolein dimethyl acetal and diphenylsilane was obtained, and aqueous hydrolysis converted it to bis-(3oxopropyl)diphenylsilane. This aldehyde underwent such rapid self-condensation that it could not be analyzed. However it reacted with the methyllithium in ether to give bis(3-hydroxybutyl)diphenylsilane, a crystalline solid.

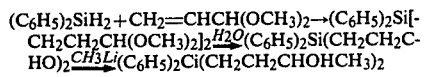

Reaction of this alcohol with phosphorous tribromide in ether gave the corresponding dibromide. Bis(3-bromobutyl)diphenylsilane underwent displacement with sodium nitrate in dimethyl sulfoxide to yield bis(3-nitrobutyl)diphenylsilane. The displacement could also be conducted in dimethyl formamide (DMF). Oxidative nitration of the salt of this nitro compound with sodium nitrite and silver nitrate, in a mixed solvent consisting of water, methanol and ether, gave bis(3,3-dinitrobutyl)diphenylsilane.

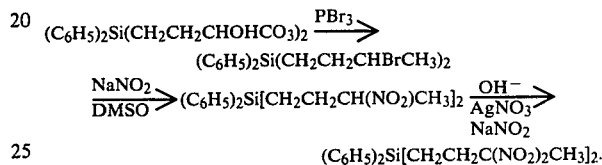

Dephenylation with bromine was similar to that used in production of the analogous fluorodinitropropyl compound. Only one phenyl group was removed readily in an inert solvent, but hydrolysis of the resulting bromosilane to silanol facilitated the removal of the second phenyl. A convenient one pot procedure utilized glacial acetic acid as a solvent for the initial bromination, with water added to complete the bromination and hydrolysis. A cyclic polysiloxane with a molecular weight between trimer and tetramer was obtained, which melted at 250°–240° C. The following examples will serve to illustrate the process of the invention, it being clearly understood however, that the conditions of the reactions described therein are by no means intended to limit the scope of this invention as defined in the claims.

EXAMPLE 1

A solution of 18.4 g (0.1 mol) of diphenylsilane, 22 g (0.215 mol) of acrolein dimethyl acetal and 0.01 g of tris(triphenylphosphine)rhodium chloride in 25 ml of benzene was refluxed for 4 hours. An additional 0.01 g of catalyst was added and the solution was refluxed for 2 hours. The solvent was stripped under vacuum and the residue was added to a mixture of 100 ml of water, 20 ml of ethanol, 0.5 ml of concentrated hydrochloric acid and 0.2 g of potassium iodide. Ethanol and methanol were distilled off slowly until the head temperature reached 80° C. The mixture was cooled and the product was extracted with three 50 ml portions of ether, dried and stripped of solvent. The aldehyde, which polymerized on standing, was dissolved immediately in 50 ml of ether and the solution was added dropwise to 150 ml of 1.5 M methyllithium in ether. The mixture was refluxed for 15 min, cooled and acidified with 10% hydrochloric acid. The ether layer was separated, washed with 50 ml of water, dried and stripped. Bis(3-hydroxybutyl)diphenylsilane (27%, mp 91°–20° C.) was isolated by crystallization from carbon tetrachloride.

EXAMPLE 2

A solution of 9.0 g (0.0275 mol) of bis(3-hydroxybutyl)diphenylsilane and 8.6 g (0.032 mol) of phosphorous tribromide in 30 ml of ether was stirred at ambient temperature for 90 hours. The solution was added to 100 ml of ice-water and the product was extracted with three 30 ml portions of carbon tetrachloride. The organic layers were washed with water, dried and stripped of solvent. The product was purified by column chromatography (silica gel and carbon tetrachloride) followed by crystallization from Skelly F, to give 6.5 g (48%) bis(3-bromopropyl)diphenylsilane, mp 61°–20° C.

EXAMPLE 3

A solution of 6.0 g (13.0 mmol) of bis(3-bromobutyl)diphenylsilane and 12.0 g (174 mmol) of sodium nitrite in 30 ml of dimethyl sulfoxide was stirred for 3 hours at 25° C. The solution was added to 250 ml of water and extracted with three 25 ml portions of carbon tetrachloride. The combined organic layers were washed with water, dried and stripped of solvent. Column chromatography and crystallization from carbon tetrachloride and Skelly F, yielded 1.5 g (29%) of bis(3-nitrobutyl)diphenylsilane, with a melting point of 84°–5° C.

EXAMPLE 4

Bis(3-nitrobutyl)diphenylsilane (1.2 g, 3.1 mmol) was dissolved, with stirring at 70° C., in a mixture of 5 ml of methanol, 13 ml of water and 6.2 mmol of potassium hydroxide. The solution was cooled to room temperature and 2.2 g (6.2 mmol) of sodium nitrite was added. The resulting solution was added quickly to a vigorously stirred mixture of 2.2 g (13 mmol) of silver nitrate, 15 ml of water and 20 ml of ether. After 5 minutes, an additional 25 ml of ether was added and the mixture was stirred for 2 hours. A saturated sodium chloride solution in water (10 ml) was added and the mixture was filtered. The precipitate was washed with ether, and the combined ether layers were dried and solvent was evaporated. Column chromatography (silica gel, methylene chloride) and crystallization (carbon tetrachloride, Skelly F) gave a yield of 0.90 g (61%) of bis(3,3-dinitrobutyl) diphenylsilane. The melting point was measured and found to be 70°–1° C.

EXAMPLE 5

A solution of 3.0 g (6.3 mmol) of bis(3,3-dinitrobutyl)diphenylsilane and 1 ml (18 mmol) of bromine in 20 ml of glacial acetic acid was refluxed for 30 minutes. Water (100 ml) was added and the mixture was refluxed for 10 minutes. The solution was cooled to room temperature and 20 ml of methylene chloride was added. A fine white precipitate was filtered and the methylene chloride layer dried, and one drop of triethylamine was added. After 24 hours, additional precipitate was isolated by filtration to give a total of 1.1 g (70%) of a mixture of cyclic bis(3,3-dinitrobutyl)polysilanes. Melting point with decomposition was measured and found to be 240°–250° C.

Processes of this invention may be carried out continuously, semi-continuously or in a batchwise fashion using commercially available equipment and materials. As it will be appreciated by those skilled in the art, many obvious variations modifications may be made in the process of this invention which are nevertheless obvious from the disclosure herein and fall within the scope of this invention.

For use as an explosive bis(3,3-dinitrobutyl)polysiloxane is loaded into conventional containers such as bombs or shells. The explosive can be detonated by conventional means used for high explosives such as booster caps ignited by electric current or power trains.

What is claimed is:

1. The compound bis(3,3-dinitrobutyl)polysiloxane represented by the structure:

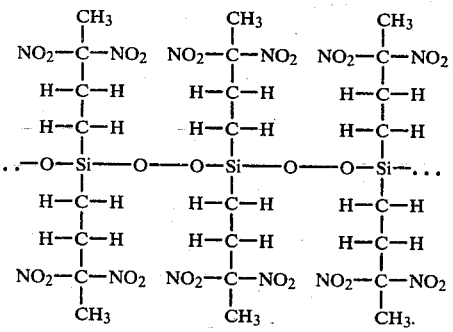

2. The compound of claim 1 wherein the molecular weight is between 1014 and 1352.

3. A process for the manufacture of bis(3,3-dinitrobutyl)polysiloxane comprised of the steps of:

reacting diphenylsilane with acrolein dimethyl acetal in the presence of a catalyst to form an addition product;

hydrolyzing the addition product to form an aldehyde;

further reacting the aldehyde with organo metallic compound to form bis(3-hydroxybutyl)diphenylsilane;

halogenating bis(3-hydroxybutyl)diphenylsilane to form a halide;

displacing the halogen group with a nitro group to form bis(3-nitrobutyl)diphenylsilane; oxidatively nitrating bis(3-nitrobutyl)diphenylsilane to form bis(3,3-dinitrobutyl)diphenylsilane; and polymerizing bis(3,3-dinitrobutyl)diphenylsilane to form bis(3,3-dinitrobutyl)polysiloxane.

4. A process for the manufacture of bis(3,3-dinitropropyl)polysiloxane as in claim 3 wherein in the reaction of diphenylsilane and acrolein dimethyl acetal the catalyst is tris(triphenylphosphine)rhodium chloride.

5. A process for the manufacture of bis(3,3-dinitropropyl)polysiloxane as in claim 3 wherein in the reaction of diphenylsilane and acrolein dimethyl acetal the catalyst is chloroplatinic acid.

6. A process for the manufacture of bis(3,3-dinitrobutyl)polysiloxane as in claim 3 wherein the organo metallic compound reacted with the aldehyde is methyllithium.

7. A process for the manufacture of bis(3,3-dinitrobutyl)polysiloxane as in claim 3 wherein the organo metallic compound reacted with the aldehyde is methyl magnesium halide.

8. A process for the manufacture of bis(3,3-dinitrobutyl)polysiloxane as in claim 3 wherein the displacement of the halogen group with a nitro group is conducted in dimethyl sulfoxide.

9. A process for the manufacture of bis(3,3-dinitrobutyl)polysiloxane as in claim 3 wherein the displacement of the halogen group with a nitro group is conducted in dimethyl formamide.

10. A process for the manufacture of bis(3,3-dinitrobutyl)polysiloxane as in claim 3 wherein the polymerization is accomplished by the use of bromine as a dephenylation reagent.

11. A process for the manufacture of bis(3,3-dinitrobutyl)polysiloxane as in claim 3 wherein the polymerization is accomplished by the use of aluminum trichloride $AlCl_3$ as a dephenylation reagent.

* * * * *